(12) United States Patent
Vogel et al.

(10) Patent No.: US 6,476,277 B2
(45) Date of Patent: Nov. 5, 2002

(54) PROCESS FOR PREPARING HYDROXYAROMATICS

(75) Inventors: Bernd Vogel, Nürnberg (DE); Elias Klemm, Nürnberg (DE); Mathias Seitz, Buckenhof (DE); Jochen Heller, Uttenreuth (DE); Jörg Reiser, Bayreuth (DE)

(73) Assignee: Bayer Aktiengesellschafter, Leverkusen (DE)

( * ) Notice: Subject to any disclaimer, the term of this patent is extended or adjusted under 35 U.S.C. 154(b) by 0 days.

(21) Appl. No.: 09/915,079

(22) Filed: Jul. 24, 2001

(65) Prior Publication Data

US 2002/0115889 A1 Aug. 22, 2002

(30) Foreign Application Priority Data

Jul. 28, 2000 (DE) .......................................... 100 36 953

(51) Int. Cl.$^7$ ................................................ C07C 37/00
(52) U.S. Cl. ..................... 568/800; 558/424; 568/705; 568/730; 568/774; 568/775; 568/780
(58) Field of Search ................................ 568/800, 775, 568/774, 730, 780, 705; 558/424

(56) References Cited

U.S. PATENT DOCUMENTS

| 4,851,605 | A | | 7/1989 | Bortinger et al. ............ 585/640 |
|---|---|---|---|---|
| 5,110,995 | A | | 5/1992 | Kharitonov et al. ......... 568/800 |
| 5,672,331 | A | | 9/1997 | Verduijn ...................... 423/702 |
| 5,672,777 | A | * | 9/1997 | Kharitonov |
| 6,414,197 | B1 | * | 7/2002 | Kustov |
| 2002/0026085 | A1 | * | 2/2002 | Chernyavsky |

FOREIGN PATENT DOCUMENTS

| DE | 196 34 406 | 11/1998 |
|---|---|---|
| EP | 0 889 081 | 1/1999 |
| EP | 0 899 018 | 1/1999 |

* cited by examiner

Primary Examiner—Michael L. Shippen
(74) Attorney, Agent, or Firm—Joseph C. Gil; Richard E. L. Henderson

(57) ABSTRACT

The present invention relates to a process for preparing hydroxyaromatics by oxidizing aromatics with dinitrogen monoxide in the gas phase in the presence of nanocrystalline zeolites.

11 Claims, No Drawings

PROCESS FOR PREPARING HYDROXYAROMATICS

BACKGROUND OF THE INVENTION

The present invention relates to a process for preparing hydroxyaromatics by oxidizing aromatics with dinitrogen monoxide in the gas phase in the presence of nanocrystalline zeolites.

Hydroxyaromatics are valuable intermediates in organic chemistry that are used for synthesizing numerous further intermediates and end products. Hydroxybenzenes are used in photography, as antioxidants, and as stabilizers in plastics. Phenol, for example, is further processed to form phenol resins, caprolactam, bisphenol A, adipic acid, or alkylphenols. Cresols are used for preparing antioxidants, herbicides, insecticides, dyes, and also odorants and flavorings. Among the three cresol isomers, p-cresol is, from economic aspects, the methylphenol of most interest. p-Cresol is used for synthesizing plastics, lubricating oils, medicaments, and nutraceuticals and for preparing perfumes and flavorings. However, it is predominantly used for producing BHT (2,6-di-tert-butyl-4-hydroxy-toluene), an important anti-aging agent and antioxidant.

A number of processes exist for preparing hydroxyaromatics. Thus, there currently exist, for example, four important industrial processes for synthesizing cresol, which are based on two synthesis routes: either toluene is hydroxylated or phenol is alkylated.

Cresol is produced from alkaline melts of toluene-sulfonates in four reaction steps. Toluene is first sulfonated by concentrated sulfuric acid, and the resultant sulfonic acid mixture is neutralized with sodium sulfite or sodium hydroxide solution and then fused with sodium hydroxide at approximately 300° C. An aqueous solution of the melt is then acidified with sulfur dioxide or sulfuric acid, which releases the cresols. Generally, a cresol mixture is produced comprising 6 to 12% o-cresol, 6 to 12% m-cresol and 80 to 85% p-cresol. The p-cresol can be separated off by means of fractional crystallization. However, this process has the disadvantage that large amounts of sodium sulfite are produced that must be disposed of.

Chlorotoluene hydrolysis is used especially for m-cresol production. In the first step, toluene is chlorinated in the presence of iron chlorides and disulfur dichloride, an o/p-chlorotoluene mixture in a ratio of 1:1 being formed. If the hydrolysis with sodium hydroxide solution is carried out directly thereafter, o-, m-, and p-cresols are produced in a ratio of 1:2:1. After rectification, an o-cresol fraction is obtained therefrom together with a poorly separable m/p-cresol mixture in a ratio of 3:1. For this reason, the chlorotoluene isomers are usually isolated and separated and only then hydrolyzed. From o-chlorotoluene, after hydrolysis and subsequent distillation, pure o- and m-cresol can be produced but p-chlorotoluene still forms a 1:1 mixture of m- and p-cresol. Disadvantages in this process are, in addition to the low yield of p-cresol, the production of by-products, such as tolyl cresols and tolyl ethers.

In the three-stage cymene hydroperoxide cleavage, toluene is alkylated with propene in the first step, forming an isomeric mixture of the cymenes. These are then oxidized with oxygen to cymene hydroperoxides that are cleaved in a third step by acid catalysis to form m/p-cresol in a ratio of 3:2 and acetone. In addition a multiplicity of by-products are formed. This process produces a distribution of isomers of 3% o-cymene, 64% m-cymene, and 33% p-cymene. The yields are low, which is principally due to the low oxidation rates of the cymenes, which only permit oxidation rates of 20% for a reasonable production of by-products. In addition, the requirements for separation and for wastewater treatment are high. In addition, the acetone formed in equivalent amounts to the cresol greatly affects the economic efficiency of the process.

Cresol synthesis by methylation of phenol is carried out both in the gas phase and in the liquid phase. Compared with toluene, phenol is a relatively expensive starting material and gives only a very low yield, to none at all, of p-cresol. A further disadvantage of the single-stage alkylation of phenol is the very high separation requirement for the product mixtures, since their components have boiling points that are very close together. In addition, high capital costs for corrosion-resistant plants considerably impair the economic efficiency of the process.

Since currently the industrially implemented processes give an unfavorable isomeric distribution of the cresols with respect to p-cresol, and this may only be shifted by multi-stage processes in the direction of higher p-cresol contents, a single-stage, selective p-cresol synthesis would be desirable. In this case the heterogeneously catalyzed selective oxidation of toluene with dinitrogen monoxide in the gas phase is an interesting alternative. The use of dinitrogen monoxide as oxidizing agent is a new synthesis route that, since the beginning of the 1980s, has been pursued for the direct synthesis of phenol from benzene. The reaction is catalyzed by zeolites.

DE-A-196 34 406 describes a process for reacting aromatics with dinitrogen monoxide to give the corresponding hydroxyaromatics, the catalyst used being a zeolite of the pentasil or β type that is subjected to a hydrothermal pretreatment with water vapor. In the hydroxylation of toluene, a selectivity with respect to cresol of 27% is achieved at a conversion rate of 24%. A disadvantage of this process is that the p-cresol content in the cresol fraction is only 16%.

U.S. Pat. No. 5,110,995 describes a process for toluene hydroxylation using dinitrogen monoxide that is carried out in the presence of special iron-containing zeolites in a narrow temperature range of 275 to 450° C. At a conversion rate of 48%, a selectivity with respect to cresol of 20% is achieved. The p-cresol content in the cresol fraction is 33%.

EP-A 889,081 describes a process for preparing hydroxyaromatics that is carried out in the presence of zeolites that have passed through a special two-stage calcination process. In the hydroxylation of toluene, a conversion rate of 25% and a yield with respect to cresol of 22% were achieved. No information is provided on the distribution of isomers.

There was therefore a need for a process for hydroxylating toluene with dinitrogen monoxide that gives p-cresol in high yield and selectivity.

SUMMARY OF THE INVENTION

A process has been found for preparing hydroxyaromatics comprising reacting aromatics of the formula (I)

$$Ar\text{—}R_n \qquad (I)$$

where
  Ar represents benzene or naphthalene,
  R represents Br, Cl, F, $NO_2$, CN, $NH_2$, OH, $C_1\text{–}C_6$-alkyl, or phenyl, and
  n denotes zero, 1, or 2, with dinitrogen monoxide in the gas phase in the presence of zeolites selected from the group consisting of pentasils, ferrierite, and zeolite-β, wherein the zeolites have a crystallite size <100 nm and are calcined at temperatures of 500 to 1350° C. before use.

DETAILED DESCRIPTION OF THE INVENTION

In the inventive process, aromatics of the formula (I) are used. These are unsubstituted or substituted benzene or unsubstituted or substituted naphthalene. Preferably, benzene, $C_1-C_6$-alkylbenzene, chlorobenzene, fluorobenzene, benzonitrile, naphthalene, or biphenyl are used. Particularly preferably, $C_1-C_6$-alkylbenzene is used, very particularly preferably toluene is used.

Hereinafter, the inventively used zeolites are described in more detail. In general, zeolites are crystalline aluminosilicates that have a highly ordered structure having a rigid three-dimensional network of $SiO_4$ and $AlO_4$ tetrahedra, which are joined by shared oxygen atoms. The electrovalency of the aluminum-containing tetrahedra is equalized by including cations in the crystal, for example, by those of the first, second, or third main group of the Periodic Table of the Elements, or by hydrogen ions. Cation exchange is possible. The spaces between the tetrahedra are occupied by water molecules before dehydration by drying or calcination.

In the inventive process, nanocrystalline zeolites from the group consisting of pentasils, β-zeolite, and ferrierite are used, these zeolites have a crystallite size <100 nm.

Zeolite-β, as basic building block, has 4-, 5-, and 6-membered rings made up of $SiO_4$ tetrahedra, which form a three-dimensional structure. This three-dimensional framework generates channels, made up of 12 rings, that are straight in two directions in space and in the form of a sine wave in the third direction in space. The material forms ellipsoidal pores having a diameter of approximately 5.5× 7.6 Å.

In addition, zeolites of the pentasil type are used for the inventive process. These, as basic building block, have a 5-membered ring made up of $SiO_4$ tetrahedra. They are characterized by a high Si/Al ratio and by pore sizes that, at dimensions of approximately 5.3×5.6 Å and 5.1×5.5 Å, are below that of zeolite-β and are in the range of the molecular sizes of the cresols. A preferred pentasil zeolite is ZSM-5.

Ferrierite, as basic building block, has 8- and 10-membered rings made up of $SiO_4$ tetrahedra. The channels are ellipsoidal, and the dimension in the [001]-plane is approximately 4.2×5.4 Å (10-membered rings), the dimension in the [010]-plane is approximately 4.8×3.5 Å (8-membered rings).

For the inventive process, in the zeolites, instead of aluminum and silicon, one or more other elements can be incorporated into the lattice. Thus aluminum can be replaced by elements such as B, Ga, Fe, Cr, V, As, Sb, Bi, Be, and their mixtures, and silicon can be replaced by a tetravalent element such as Ge, Ti, Zr, Hf, or their mixtures.

Preferably, in the inventive process the above-mentioned zeolites are used in an acid form. The acid forms of the zeolites are preferably prepared by exchanging cations for ammonium ions or by exchange with mineral acids. However, partially acid zeolites can also be used in which a portion of the hydrogen ions have been replaced by cations of the first, second, and third main group of the Periodic Table of the Elements and of subgroups Ia, IIa, IVa, Va, VIa, VIIa, and VIIIa. Preferred cations are cations of the elements Li, Na, K, Rb, Mg, Ca, Ba, Fe, Co, V, Zn, Cr, Mn, Ni, Pd, and Cu, and particularly preferred cations are cations of the elements Li, K, Rb, Mg, Ca, Ba, Fe, Co, V, Ni, and Zn. Preferably, in the inventive process, zeolites in which 50 to 100% (particularly preferably 80 to 100%) of the cations originally present are exchanged by hydrogen ions.

The zeolites used in the inventive process preferably have an Si/Al ratio of 15 to 400, preferably 20 to 200, and particularly preferably 25 to 180.

The zeolites that are used in the inventive process and that have a crystallite size <100 nm can be prepared, for example, as described in WO 93/08124 or in EP-A 178,687. The crystallite size in the zeolites used in the inventive process is preferably 20 to 100 nm, particularly preferably between 30 and 40 nm.

The zeolites used in the inventive process are calcined before their use. They are calcined at a temperature of 500 to 1350° C., preferably 500 to 1250° C., particularly preferably at a temperature of 700 to 1200° C. The calcination is preferably carried out over a period of 0.5 to 18 hours, preferably from 1 to 10 hours. The calcination preferably takes place in a nitrogen or nitrogen/oxygen atmosphere having an oxygen content of preferably 1 to 50% by volume (particularly preferably from 10 to 30% by volume), in a dinitrogen oxide atmosphere, or in air. Very particularly preferably, the zeolites are calcined in air at 700 to 1200° C. over a period of 1 to 10 hours.

In the inventive process, the zeolites can be used in the form of powders, granules, or particles or in extrudate form. In addition, the zeolites used in the inventive process can be embedded in an inorganic matrix that is preferably inert. Suitable inorganic matrix materials are, for example, conventional support materials such as silica, aluminum oxide, zirconium oxide, aluminosilicates, synthetic porous materials, or clay. Preferably, non-acid support materials are used.

In the inventive process the loading of the catalyst with aromatic, expressed by the WHSV (Weight Hourly Space Velocity; kg/h of aromatic per kg of catalyst), is preferably 0.1 to 10 $h^{-1}$, particularly preferably 0.2 to 5 $h^{-1}$, very particularly preferably 0.5 to 3 $h^{-1}$.

In a preferred embodiment of the inventive process, the zeolites used are subjected to a modification with silanes or boranes before the calcination. In this case silanes or boranes are preferably deposited in a CVD (chemical vapor deposition) process on the zeolites to be used. Preferably, the silanes used are disilane, alkylsilanes (for example, methylsilane or ethylsilane), or silane. The boranes used are preferably diborane and borane. The deposition is preferably performed at temperatures of 150 to 300° C., particularly preferably 200 to 270° C. Preferably, a silane/borane partial pressure of 1 to 1000 mbar (particularly preferably 350 to 650 mbar) is established. The deposition time is preferably 30 to 300 min, particularly preferably 150 to 250 min.

In a further preferred embodiment of the inventive process, the zeolites used are subjected to a modification with alkoxysilanes after the calcination. In this case the alkoxysilanes are deposited in the gas phase, preferably in the reactor in which the inventive process is carried out. Preferably $C_1-C_4$-alkoxysilanes (for example, tetramethoxysilane) are used or, particularly preferably, tetraethoxysilane is used. The deposition is preferably carried out at temperatures of 100 to 400° C., particularly preferably 150 to 250° C. Preferably, an alkoxysilane partial pressure of 1 to 500 mbar (particularly preferably 10 to 100 mbar) is established. The deposition time is preferably 5 to 180 min, particularly preferably 10 to 80 min. The deposition preferably takes place in a plurality of cycles; preferably 5 to 25 deposition cycles are carried out. Particularly preferably, the deposition is carried out in such a manner that tetraethoxysilane at a partial pressure of 30 to 60 mbar is deposited in 10 to 20 deposition cycles at 180 to 220° C. at a cycle time of 20 to 40 min. After each deposition, the zeolite is preferably thermally post-treated in an oxygen atmosphere, oxygen/air atmosphere or in air at temperatures of 200 to 600° C.

The reaction temperatures in the inventive process are preferably 300 to 560° C., preferably 350 to 540° C., very particularly preferably 400 to 500° C.

The operating pressure is preferably between 0.1 and 15 bar, particularly preferably between 0.2 and 6 bar, very particularly preferably between 0.5 and 2 bar.

The molar ratio of aromatic:dinitrogen monoxide is preferably 12:1 to 1:10, particularly preferably 10:1 to 1:5, very particularly preferably 8:1 to 1:4.

The reaction usually takes place in the gas phase.

The reaction of the aromatics and the calcination of the zeolites and any modification of the zeolites with alkoxysilanes to be carried out for the present invention can be carried out in a conventional reactor suitable for heterogeneous catalysis, for example, in a fixed-bed reactor or a fluidized-bed reactor.

Fixed-bed reactors that can be used are, for example, loop reactors, shelf reactors, and in particular tubular reactors. If the reaction is carried out in a fixed-bed reactor, the use of zeolite catalysts that have a mean particle diameter of 500 to 2000 μm has proved to be particularly expedient.

The fluidized-bed reactor has a reaction space in which a granular bed of solids is loosened by a gas flowing through from below and is maintained in this suspended state. This highly loosened gas-permeable bed is termed a fluidized bed. It has a similar behavior to a boiling liquid with intensive mixing. In the fluidized-bed process, the individual components can be passed mixed or separately via a pre-evaporator or directly into the fluidized bed. The use of zeolite catalyst in extruded form having a mean particle diameter of 80 to 250 μm has proved to be particularly expedient in this case.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

Catalyst Preparation

The following catalysts were used:

A: Zeolite catalyst of the H[Al]ZSM-5 type, Si/Al ratio: 15

B: Zeolite catalyst of the H[Al]ZSM-5 type, Si/Al ratio: 28

C: Zeolite catalyst of the H[Al]ZSM-5 type, Si/Al ratio: 113

D: Zeolite catalyst of the Hβ type, Si/Al ratio: 75

E: Zeolite catalyst of the H[Al]ZSM-5 type, Si/Al ratio: 25, crystallite size: 1000–3000 nm F: Zeolite catalyst of the H[Al]ZSM-5 type, Si/Al ratio: 26, crystallite size: 30–40 nm The zeolites were compressed without binder to form tablets 0.5 cm in diameter and were then comminuted and fractionated to a particle size of 1.0 to 1.4 mm.

Examples 2 to 4 (Comparison)

In Examples 2 to 4 in each case 2 g of the above-described catalysts were used in a fixed-bed reactor at 450° C. for the reaction of toluene with dinitrogen monoxide. The length of the bed was 20 to 30 cm. The WHSV was selected to be 2.5 $h^{-1}$ (g of toluene/h and g of catalyst). Toluene and dinitrogen monoxide were used in a molar ratio of 1:3. All samples were taken after 32 min TOS (time on stream) and analyzed by gas chromatography using a CP-Chirasil-Dex® column. The results are given in Table 1.

TABLE 1

| Example | Crystallite size [nm] | Zeolite | Degree of conversion of toluene [%] | Selectivity with respect to cresol [%] | p-Cresol content [%] |
|---|---|---|---|---|---|
| 2 (comp) | 20–100 | A | 4.9 | — | — |
| 3 (comp) | 20–100 | B | 9.6 | 11.0 | 8.9 |
| 4 (comp) | 20–100 | C | 3.0 | 30.0 | 16.5 |

Examples 5 to 7

Examples 5 to 7 were carried out in a similar manner to Examples 2 to 4 except that the catalysts B, E, and F were calcined for 2 h at 900° C. in air before the reaction. The results are given in Table 2.

TABLE 2

| Example | Crystallite size [nm] | Zeolite | Degree of conversion of toluene [%] | Selectivity with respect to cresol [%] | p-Cresol content [%] |
|---|---|---|---|---|---|
| 5 (comp) | 1000–3000 | E | 4.5 | 21.0 | 34.0 |
| 6 | 20–100 | B | 14.0 | 33.0 | 23.0 |
| 7 | 30–40 | F | 18.7 | 39.0 | 35.0 |

Examples 8 to 11

Examples 8 to 11 were carried out in a similar manner to Examples 2 to 4 except that the catalysts were calcined for 2 hours at 1000° C. in air before the reaction. The results are given in Table 3.

TABLE 3

| Example | Crystallite size [nm] | Zeolite | Degree of conversion of Toluene [%] | Selectivity with respect to cresol [%] | p-Cresol content [%] |
|---|---|---|---|---|---|
| 8 | 20–100 | A | 10.0 | 23.9 | 17.8 |
| 9 | 20–100 | B | 15.6 | 29.3 | 29.1 |
| 10 | 20–100 | C | 12.3 | 58.1 | 45.4 |
| 11 | 20–100 | D | 11.0 | 63.0 | 46.0 |

Examples 12

Catalyst B was treated for 3 hours at 200° C., with silane (partial pressure 500 mbar) for a period of 200 min and was then calcined at 1000° C. for 2 hours in air. The crystallite size was 20 to 100 nm. Toluene was reacted with dinitrogen monoxide in a similar manner to Examples 2 to 4. A degree of conversion of toluene of 16.0%, a selectivity of 47.0%, and a p-cresol content of 44.0% were achieved.

Example 13

Catalyst C was calcined in air at 1100° C. for 2 hours and was then treated with tetraethoxysilane (partial pressure 40 mbar) in 14 cycles, each of 30 min at 200° C. After each deposition cycle, the catalyst was thermally post-treated in air for 2 hours at 500° C. The crystallite size was 20 to 100 nm. The toluene was reacted with dinitrogen monoxide in a similar manner to Examples 2 to 4. A degree of conversion of toluene of 6.0%, a selectivity of 60.0%, and a p-cresol content of 57.0% were achieved.

What is claimed is:

1. A process for preparing hydroxyaromatics comprising reacting aromatics of the formula (I)

$$Ar-R_n \qquad (I)$$

wherein
Ar represents benzene or naphthalene,
R represents Br, Cl, F, $NO_2$, CN, $NH_2$, OH, $C_1$–$C_6$-alkyl, or phenyl, and
n denotes zero, 1, or 2,
with dinitrogen monoxide in the gas phase in the presence of zeolites selected from the group consisting of pentasils, ferrierite and zeolite-β wherein the zeolites have a crystallite size <100 nm and are calcined at temperatures of 500 to 1350° C. before use.

2. A process according to claim 1 for preparing a $C_1$–$C_6$-hydroxyalkylbenzene having an increased content of p-isomer from a $C_1$–$C_6$-alkylbenzene.

3. A process according to claim 1 for preparing a cresol having an increased content of p-cresol from toluene.

4. A process according to claim 1 wherein the zeolite is in an acid form.

5. A process according to claim 1 wherein the calcination is carried out over a period of 0.5 to 18 hours.

6. A process according to claim 5 wherein the calcination is carried out under a nitrogen or a nitrogen/oxygen atmosphere, in a dinitrogen oxide atmosphere, or in air.

7. A process according to claim 1 wherein the zeolite has a crystallite size of 20 to 100 nm.

8. A process according to claim 1 wherein the zeolite has a crystallite size of 30 to 40 nm.

9. A process according to claim 1 wherein the zeolite is H[Al]ZSM-5 or H-β.

10. A process according to claim 1 wherein the zeolite is modified by deposition of silanes or boranes before the calcination.

11. A process according to claim 1 wherein the zeolite is modified by deposition of alkoxysilanes after calcination.

* * * * *